United States Patent
Wang et al.

(10) Patent No.: US 11,684,591 B2
(45) Date of Patent: *Jun. 27, 2023

(54) USE OF A $GABA_A$ RECEPTOR ALLOSTERIC ENHANCER IN MEDICINE

(71) Applicant: XI'AN LIBANG ZHAOXIN BIOTECHNOLOGY CO., LTD., Xi'an (CN)

(72) Inventors: Rutao Wang, Xi'an (CN); Long An, Xi'an (CN); Yi Zhao, Xi'an (CN); Jinghua Pang, Xi'an (CN); Tao Chen, Xi'an (CN); Weijiao Wang, Xi'an (CN)

(73) Assignee: XI'AN LIBANG ZHAOXIN BIOTECHNOLOGY CO., LTD, Xi'an (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/271,828

(22) PCT Filed: Jul. 10, 2019

(86) PCT No.: PCT/CN2019/095395
§ 371 (c)(1),
(2) Date: Feb. 26, 2021

(87) PCT Pub. No.: WO2020/042767
PCT Pub. Date: Mar. 5, 2020

(65) Prior Publication Data
US 2021/0315835 A1 Oct. 14, 2021

(30) Foreign Application Priority Data
Aug. 31, 2018 (CN) .......................... 201811011320.1

(51) Int. Cl.
*A61K 31/05* (2006.01)
*A61P 25/08* (2006.01)

(52) U.S. Cl.
CPC .............. *A61K 31/05* (2013.01); *A61P 25/08* (2018.01)

(58) Field of Classification Search
CPC ................................ A61K 31/05; A61P 25/08
See application file for complete search history.

(56) References Cited

U.S. PATENT DOCUMENTS

| | | | |
|---|---|---|---|
| 10,329,243 B2 * | 6/2019 | Wang ...................... C07C 25/18 |
| 2018/0141895 A1 | 5/2018 | Wang et al. | |
| 2018/0185299 A1 | 7/2018 | Wang et al. | |

FOREIGN PATENT DOCUMENTS

| | | |
|---|---|---|
| CN | 101792462 A | 8/2010 |
| CN | 101804043 A | 8/2010 |
| CN | 105250316 A | 1/2016 |
| CN | 107556191 A | 1/2018 |
| EP | 2960225 A1 | 12/2015 |
| EP | 3246304 A2 | 11/2017 |
| JP | 2015521633 A | 7/2015 |
| JP | 2018503637 A | 2/2018 |

OTHER PUBLICATIONS

Teocchi et al., "Hippocampal gene expression dysregulation of Klotho, nuclear factor kappa B and tumor necrosis factor in temporal lobe epilepsy patients," J. Neuroinflammation May 1, 2013;10:53. PMID: 23634661. (Year: 2013).*
First Office Action issued for corresponding Japanese Patent Application 2021-536133 dated Apr. 26, 2022, 8 pages.
Extended European Search Report dated Apr. 25, 2022 for counterpart European patent application No. 19856003.9, 7 pages.
Extended European Search Report dated Apr. 28, 2022 for counterpart European patent application No. 19856387.6, 7 pages.
PCT International Search Report for International Application No. PCT/CN2019/095395, dated Sep. 2, 2019, 8 pages.
Lake et al., "The effects of delayed reduction of tonic inhibition on ischemic lesion and sensorimotor function," Journal of Cerebral Blood Flow & Metabolism, 2015, vol. 35, pp. 1601-1609.
First Office Action dated Jul. 5, 2022 for counterpart Chinese patent application No. 201811011320.1, 15 pages.
Search Report dated Jul. 5, 2022 for counterpart Chinese patent application No. 201811011320.1, 4 pages.

* cited by examiner

*Primary Examiner* — Theodore R. Howell
(74) *Attorney, Agent, or Firm* — Hoffman Warnick. LLC

(57) ABSTRACT

An application of a $GABA_A$ receptor allosteric enhancer in medicine. Specifically provided is use of the $GABA_A$ receptor allosteric enhancer shown in formula (I) in preparation of drugs for sedatives, hypnosis, treatment or prevention of anxiety, depression, insomnia, nausea, vomiting, migraine, schizophrenia, convulsions, and epilepsy.

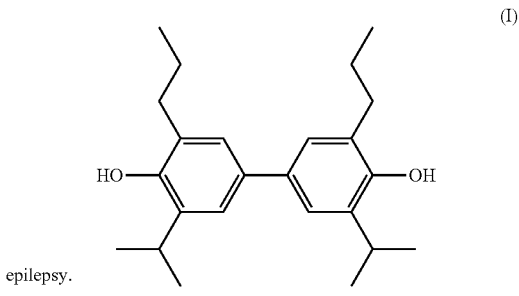

(I)

3 Claims, 2 Drawing Sheets

USE OF A GABA$_A$ RECEPTOR ALLOSTERIC ENHANCER IN MEDICINE

CROSS-REFERENCE TO RELATED APPLICATIONS

This application is a National Stage of International Application No. PCT/CN2019/095395, filed Jul. 10, 2019, which claims priority to Chinese Patent Application No. 201811011320.1, filed Aug. 31, 2018, both of which are hereby incorporated by reference in their entireties.

TECHNICAL FIELD

This disclosure relates to the field of medicine, specifically, to the use of a GABA$_A$ receptor allosteric enhancer in medicine.

BACKGROUND

Epilepsy is a chronic condition in which sudden abnormal discharge of neurons in the brain causes transient brain dysfunction. Seizures are clinical phenomena caused by brain neuron abnormality and excessive hyper-synchronized discharge. Due to the increasing prevalence of epilepsy patients in China and abroad, epilepsy is a growing health concern in the society. Statistics show that epilepsy sufferers account for about 0.5% to 1% of the world's population. Despite of ongoing and in-depth studies of epilepsy, little is known about the pathogenesis of epilepsy, while the drugs currently used only partially relieve the condition of patients with epilepsy and are only 60 to 70 percent effective in patients with developing major episodes.

In recent years, with the development in epilepsy studies, it has been found that GABA$_A$ receptors are closely related to the onset of epilepsy. GABA$_A$ receptors are the most important central inhibitory receptors in human central tissues, and activation of GABA$_A$ receptor in the brain can hyperpolarize neurons and reduce excitability of nerve cells. Traditional anti-epilepsy drugs, benzodiazepines and barbiturates, and newly developed and commercialized drugs like sodium valproate and levitracetam, are all associated with enhancing GABA$_A$ receptor functions or increasing tissue GABA concentration.

Chinese Patent ZL201010160034.9 discloses a dipropofol (3,3',5,5'-tetraisopropyl-4,4'-biphenol, shown in FIG. 2), a novel antiepileptic drug developed by Xi'an Libang Pharmaceutical Co., Ltd., which is a novel GABA$_A$ receptor allosteric modulation enhancer and used for the treatment of various seizures including status epilepticus. This compound shows good antiepileptic activity as well as minor side effects in pre-clinical studies and is now in the clinical research phase. However, it is found in the pre-clinical studies that this compound has a relatively slow rate in entering the brain after intravenous injection while it takes some time for the drug to reach a therapeutic threshold concentration in the brain, and is not immediately effective in seizure episodes. Thus, it is the purpose of the disclosure to develop an antiepileptic drug that acts faster with higher potency.

SUMMARY OF DISCLOSURE

An object of this disclosure is to provide the use of GABA$_A$ receptor allosteric enhancer in medicine.

To achieve the above object, in one aspect, this disclosure provides a method for treating GABA$_A$ receptor-associated diseases, wherein the method comprising administrating a GABA$_A$ receptor allosteric enhancer shown in formula (I):

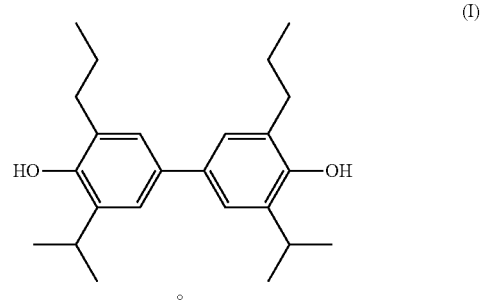 [SMILES: CCCc1cc(-c2cc(CCC)c(O)c(C(C)C)c2)cc(C(C)C)c1O]

(I)

According to some specific embodiments of this disclosure, the said treating GABA$_A$ receptor-associated diseases include sedation, hypnosis, treatment or prevention of anxiety, depression, insomnia, nausea, vomiting, migraines, schizophrenia, convulsions and epilepsy.

According to some specific embodiments of this disclosure, said epilepsy is an epilepsy that can cause neuron loss in the hippocampus.

According to some specific embodiments of this disclosure, said epilepsy is temporal lobe epilepsy.

DESCRIPTION OF EMBODIMENTS

Figure 1:
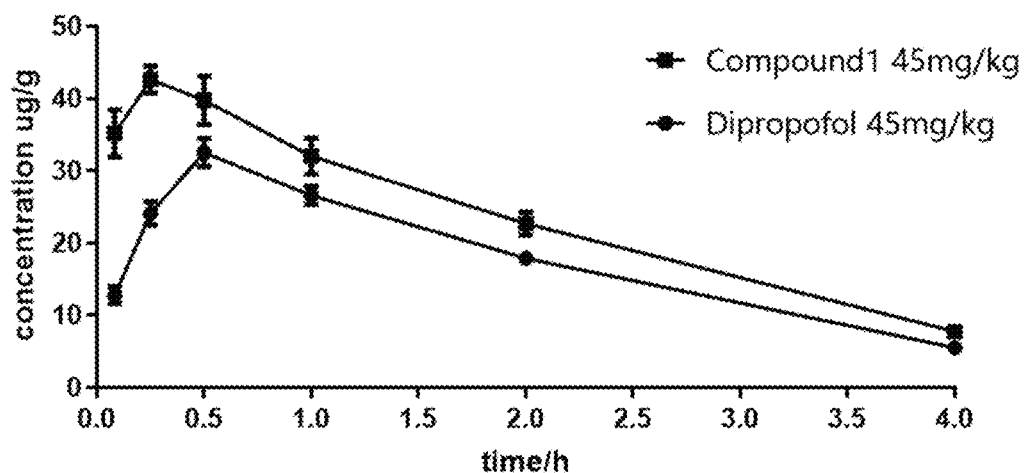
FIG. 1 is a diagram of the changes in Compound 1 and dipropofol concentrations in brain tissues at different points in time after administration in rats.

The technical solutions of the present disclosure will be described in details below in conjunction with the accompanying drawings and examples and are encompassed by, but not limiting the protection scope of this disclosure.

Example 1

Preparation of 4,4'-dihydroxy-3,3'-diisopropyl-5,5'-dipropylbiphenyl (Compound 1)

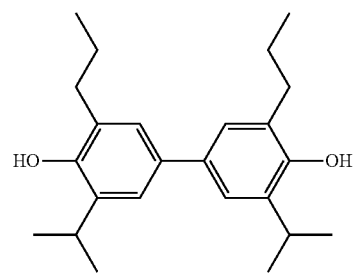 [SMILES: CCCc1cc(-c2cc(CCC)c(O)c(C(C)C)c2)cc(C(C)C)c1O]

(1) In a 25 mL round bottom flask, o-isopropyl phenol (1.0 g, 7.3 mmol) and allyl bromide (14.6 mmol) were consecutively added and dissolved with dichloromethane;

(2) In another 50 mL flask, benzyl tributyl ammonium bromide (0.26 g, 0.73 mmol) was added and dissolved with a 1M NaOH solution;

(3) At room temperature, the solution obtained in (1) was slowly added into the solution obtained in (2), and stirred at room temperature for 2 h; the organic phase was separated, and the water phase was extracted with dichloromethane; the organic phase was combined, washed with water and saturated sodium chloride, dried over anhydrous sodium sulfate, and concentrated to obtain a colorless liquid; under the protection by nitrogen, the liquid was heated at 250° C. for 2 h, and then cooled and subjected to column chromatography to obtain a colorless liquid; the colorless liquid was dissolved in anhydrous ethanol, into which Pd/C was added for reduction; after the reduction, suction filtration was carried out, and the resultant mother was concentrated to give 2-isopropyl-6-propylphenol;

$^1$H NMR (400 MHz, CDCl$_3$) δ 7.06 (dd, J=7.6, 1.6 Hz, 1H), 6.97 (dd, J=7.5, 1.6 Hz, 1H), 6.85 (t, J=7.6 Hz, 1H), 4.75 (s, 1H), 3.22-3.13 (m, 1H), 2.59-2.54 (m, 2H), 1.72-1.59 (m, 2H), 1.26 (d, J=6.9 Hz, 6H), 0.99 (t, J=7.3 Hz, 3H);

(4) 2-isopropyl-6-propylphenol (1.0 g, 5.6 mmol) was dissolved in 20 mL dichloromethane, into which a catalyst, Cu(OH)Cl.TMEDA (N,N,N,N-tetramethylethylenediamine basic copper chloride) (50 mg, 0.1 mmol), was added and stirred at room temperature to obtain a red solid quinone; then, it was reduced with sodium dithionite to give 4,4'-dihydroxy-3,3'-diisopropyl-5,5'-dipropylbiphenyl (1.1 g, 55.5%).

4,4'-dihydroxy-3,3'-diisopropyl-5,5'-dipropylbiphenyl:
$^1$H NMR (300 MHz, CdCl$_3$) δ 7.29 (s, 4H), 6.52 (s, 2H), 3.13-3.08 (m, 2H), 2.43-2.40 (m, 4H), 1.51-1.43 (m, 4H), 1.03 (d, 12H), 0.84-0.81 (m, 6H).

Experimental Example 1

1. Comparative Test of the Distribution in Brain Tissues of Compound 1 and Dipropofol (3,3', 5,5'-Tetraisopropyl-4,4'-Biphenol) after Intravenous Administration in Rats 72 SD rats, weighing 200 to 220 g, were randomly divided into 12 groups (6 per time group), and fasted for 12 h before administration. A dose of 45 mg/kg was intravenously administered with Compound 1 or the dipropofol respectively, and the rates were sacrificed at 5 min, 15 min, 30 min, 1 h, 2 h and 4 h after the administration. The brain tissues were removed immediately, rinsed with ice-cold distilled water, blotted dry, and frozen at −40° C. for storage. The concentration of Compound 1 or the dipropofol in the brain tissues at different points in time after administration in rats was measured by LC-MS/MS, as shown in Table 1 and FIG. 1.

TABLE 1

| | | Drug concentration in brain tissues (ug/g) | | | | | |
|---|---|---|---|---|---|---|---|
| | | 5 min | 15 min | 30 min | 1 h | 2 h | 4 h |
| Compound 1 | Male average | 35.19 | 42.66 | 39.78 | 32.02 | 22.67 | 7.75 |
| | Standard deviation | 3.26 | 1.89 | 3.33 | 2.49 | 1.60 | 0.66 |

TABLE 1-continued

| | | Drug concentration in brain tissues (ug/g) | | | | | |
|---|---|---|---|---|---|---|---|
| | | 5 min | 15 min | 30 min | 1 h | 2 h | 4 h |
| Dipropofol | Overall average | 12.8 | 24.1 | 32.5 | 26.6 | 17.9 | 5.52 |
| | Standard deviation | 1.19 | 1.61 | 1.99 | 1.24 | 0.61 | 0.51 |

The concentration of Compound 1 in the brain tissues at 5 min after intravenous administration was 2.75 times of that of the dipropofol, with the concentration of Compound 1 peaked at 15 min in the brains tissues and the concentration of the dipropofol peaked at 30 min after administration. The $AUC_{0-4h}$ of Compound 1 in the brain tissues was about 1.31 times of that of the dipropofol.

The above results show that after being intravenously administrated with the same dose, Compound 1 has a significantly higher brain entry rate and brain intake amount than the dipropofol.

2. In Vitro GABA$_A$ Receptor Target Affinity Test

A radioligand ([$^{35}$S] TBPS) receptor competitive binding test was used to evaluate the affinity of the test compound (10 uM) with GABA$_A$ receptors. The results are shown in Table 2 below.

TABLE 2

| Targets | Species | Test concentration (uM) | IC50 |
|---|---|---|---|
| Dipropofol | GABA$_A$, Chloride Channel, TBPS | rats | 30, 10, 3, 1, 0.3 | 2.06 uM |
| Compound 1 | GABA$_A$, Chloride Channel, TBPS | rats | 30, 10, 3, 1, 0.3 | 2.93 uM |

The results demonstrate that Compound 1 has high affinity for the GABA$_A$ receptors, which affinity is comparable to that of the dipropofol.

3. Antiepileptic Test of Compounds 1 and Dipropofol (3,3', 5,5'-Tetraisopropyl-4,4'-Biphenol) in Rats with PTZ-Induced Seizures In this test, male SD rats (Xi'an Jiaotong University), weighing 200 to 250 g, were used and intravenously administrated with 45 mg/kg of a Dipropofol injection, a Compound 1 injection, and blank solvent of the same volume. 1, 3, 5, 10, 15, 30, 60, 90 mins, and 120 mins after the intravenous administration, 70 mg/kg of PTZ was intraperitoneally injected in the rats to induce tonic-clonic seizures. 7 rats were used for each time point in each drug group. Rat seizure intensity was recorded in accordance with the Racine grading criteria in grade III to V seizure status. Scores were recorded according to the seizure intensity: 5 points for grade V, 4 points for grade IV, 3 points for grade III, and 0 point for below grade III. The seizure intensity for each group of animals was the total score of 7 animals, and the results are shown in Table 3 below.

TABLE 3

Scores of seizure grade and intensity of animals at various time points after administration for prevention purpose

| n = 7 Time point | Model Number of episodes (animals) | | | Seizure Intensity | Dipropofol Number of episodes (animals) | | | Seizure Intensity | Compound 1 Number of episodes (animals) | | | Seizure Intensity |
|---|---|---|---|---|---|---|---|---|---|---|---|---|
| | III | IV | V | | III | IV | V | | III | IV | V | |
| 1 min | 0 | 0 | 7 | 35 | 0 | 7 | 0 | 28 | 2 | 2 | 0 | 14 |
| 3 min | 0 | 0 | 7 | 35 | 2 | 5 | 0 | 26 | 0 | 0 | 0 | 0 |
| 5 min | 0 | 0 | 7 | 35 | 3 | 3 | 0 | 21 | 0 | 0 | 0 | 0 |
| 10 min | 0 | 0 | 7 | 35 | 2 | 2 | 0 | 14 | 0 | 0 | 0 | 0 |
| 15 min | 0 | 0 | 7 | 35 | 0 | 0 | 0 | 0 | 0 | 0 | 0 | 0 |
| 30 min | 0 | 0 | 7 | 35 | 0 | 0 | 0 | 0 | 0 | 0 | 0 | 0 |
| 60 min | 0 | 0 | 7 | 35 | 0 | 0 | 0 | 0 | 0 | 0 | 0 | 0 |
| 90 min | 0 | 0 | 7 | 35 | 0 | 0 | 0 | 0 | 0 | 0 | 0 | 0 |
| 120 min | 0 | 0 | 7 | 35 | 2 | 1 | 0 | 10 | 0 | 0 | 0 | 0 |

The experimental results show that 3 to 5 minutes after being intravenously injected, Compound 1 can completely inhibit PTZ-induced major seisures, and the potency can be maintained for 120 minutes or more after administration. However, it was not until 15 minutes after intravenous injection of the bisphenol that the PTZ-induced major seizures are completed inhibited, and the potency begins to decline at 90 minutes after administration. As seen from the above results, the compound of this disclosure acts at a significantly faster rate than the dipropofol, with the peak potency maintained for a duration longer than the latter.

4. KA-Induced Chronic Epilepsy Model

Figure 2:
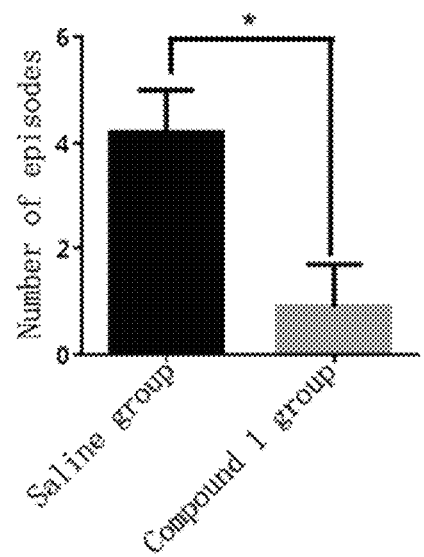
FIG. 2 provides the number of spontaneous seizure episodes in the KA-induced chronic epilepsy model in Experimental Example 1.
Figure 3:
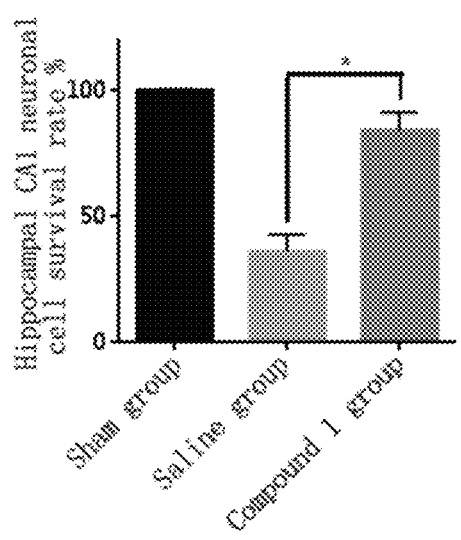
FIG. 3 is the neuronal cell survival rate of the KA-induced chronic epilepsy model in Experimental Example 1.

A chronic epilepsy animal model was established by microinjection of kainic acid (KA) in the hippocampus: 0.2 ug (2 ul) KA was injected into the hippocampus of mice by using a stereotaxic device. Within 6 hours after modeling, the mice had seizures. Within 3 weeks after modeling, the mice developed spontaneous seizures. Mice with spontaneous seizures after modeling were divided into two groups (n=10): Compound 1 administration group and saline administration group. On day 2 after modeling, Compound 1 (100 mg/kg) and saline of the same volume was intravenously administered, respectively. 3 weeks after modeling, the number of episodes of spontaneous seizures in the mice was observed for 2 weeks (FIG. 2). After the observation, the mice were sacrificed, hippocampal tissue sections were taken, and NeuN staining was used to calculate the survival rate of neurons in the CA1 area (FIG. 3).

The results show that the administration of the compound of the present disclosure in KA-induced chronic epilepsy model animals can not only significantly inhibit spontaneous seizures, but also significantly inhibit hippocampal neuron death induced by the epilepsy model.

The invention claimed is:

1. A method of treating epilepsy, comprising administering a $GABA_A$ receptor allosteric enhancer represented by formula (I):

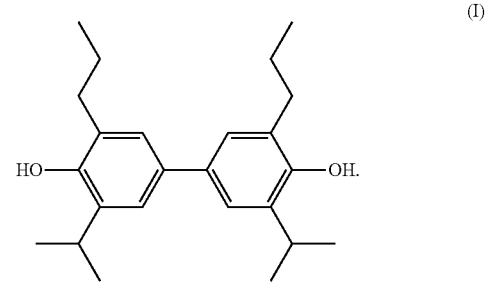 [SMILES: CCCc1cc(-c2cc(CCC)c(O)c(C(C)C)c2)cc(C(C)C)c1O]

(I)

2. The method according to claim 1, wherein the epilepsy is an epilepsy that causes neuron loss in the hippocampus.

3. The method according to claim 1, wherein the epilepsy is temporal lobe epilepsy.

* * * * *